United States Patent [19]

Pfirmann et al.

[11] Patent Number: 5,565,612
[45] Date of Patent: Oct. 15, 1996

[54] SUBSTITUTED 2-CHLORO-3,4,5-TRIFLUOROBENZENES AND A PROCESS FOR THEIR PREPARATION

[75] Inventors: Ralf Pfirmann, Griesheim; Thomas Schach, Gernsheim, both of Germany

[73] Assignee: Hoechst Aktiengesellschaft, Germany

[21] Appl. No.: 435,794

[22] Filed: May 5, 1995

[30] Foreign Application Priority Data

May 9, 1994 [DE] Germany .............. 44 16 329.0

[51] Int. Cl.$^6$ .................................. C07C 211/45
[52] U.S. Cl. .................... 564/442; 558/425; 570/127
[58] Field of Search .................. 564/442; 558/425; 570/127

[56] References Cited

U.S. PATENT DOCUMENTS

| | | | |
|---|---|---|---|
| 5,041,674 | 8/1991 | Pews et al. | 570/127 X |
| 5,072,038 | 12/1991 | Klauke et al. | 558/425 X |
| 5,162,584 | 11/1992 | Moilliet et al. | 564/442 |
| 5,332,851 | 7/1994 | Kumai et al. | 570/127 X |
| 5,349,098 | 9/1994 | Kumai et al. | 570/127 X |
| 5,399,767 | 3/1995 | Nasu et al. | 564/442 X |

FOREIGN PATENT DOCUMENTS

| | | | |
|---|---|---|---|
| 0433124 | 6/1991 | European Pat. Off. | 558/425 |
| 0447259 | 9/1991 | European Pat. Off. . | |
| 0497239 | 8/1992 | European Pat. Off. | 558/425 |
| 0600317 | 6/1994 | European Pat. Off. . | |
| 4123322 | 1/1993 | Germany . | |

OTHER PUBLICATIONS

Chemical Abstracts, vol. 117, No. 23, Dec. 7, 1992, *Preparation of 2–chloro–3,4,5–trifluorobenzoic acids*, 233606b.
Wray, et al.; J.C.S. Perkin II (1976), pp. 1307–1312.
C.A., 18525d (1966) vol. 65, Imperial Smelting Corp.

*Primary Examiner*—Robert Gerstl
*Attorney, Agent, or Firm*—Connolly and Hutz

[57] ABSTRACT

The present invention relates to substituted 2-chloro-3,4,5-trifluorobenzenes of the formula

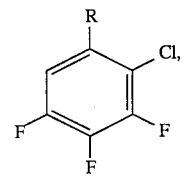

in which R is $NO_2$, $NH_2$, CN or Cl, and to a process for the preparation of substituted 2-chloro-3,4,5-trifluorobenzenes of the formula given above, in which R is $NO_2$, $NH_2$, CN, Cl or Br, which involves reacting 2,3,4-trifluorochlorobenzene with a nitrating agent in the presence or absence of a water-insoluble solvent at from −10° C. to 50° C., reducing 2-chloro-3,4,5-trifluoronitrobenzene or a mixture which contains 2-chloro-3,4,5-trifluoronitrobenzene and 5-chloro-2,3,4-trifluoronitrobenzene, in the presence of an organic solvent, isolating 2-chloro-3,4,5-trifluoroaniline or a mixture which contains 2-chloro-3,4,5-trifluoroaniline and 5-chloro-2,3,4-trifluoroaniline, diazotizing this product, if desired, and exchanging the diazotized group for a chloride atom, bromide atom or cyanide radical.

1 Claim, No Drawings

SUBSTITUTED 2-CHLORO-3,4,5-TRIFLUOROBENZENES AND A PROCESS FOR THEIR PREPARATION

The present invention relates to new substituted 2-chloro-3,4,5-trifluorobenzenes, specifically 2-chloro-3,4,5-trifluoronitrobenzene, 2-chloro-3,4,5-trifluoroaniline, 2-chloro-3,4,5-trifluorobenzonitrile and 2-chloro-3,4,5-trifluorochlorobenzene, and to a process for their preparation.

The new compounds according to the invention are valuable intermediates for the production of modern, highly effective antibacterial agents from the series of the 6-fluoro-8-haloquinolonecarboxylic acids.

6-Fluoro-8-haloquinolonecarboxylic acids can be prepared by methods known from the literature (EPA-0 198 192, EP-A-0 357 047) starting from 2,3-dihalo-4,5-difluorobenzoic acids. In this context the nature of the halogen atom in position 2, the position which is significant for the required cyclization, of the 2,3-dihalo-4,5-difluorobenzoic acid is not important. A fluorine atom in position 2 has the advantage that it can be substituted with ease, but the introduction of a fluorine atom into this position is always associated with increased technical complexity and, accordingly, with costs. It could therefore be of particular advantage to substitute, instead of a fluorine atom, a chlorine atom in position 2 with cyclization.

2,3,4,5-Tetrafluorobenzoic acid has hitherto been employed as starting material for the preparation of 6,8-difluoroquinolonecarboxylic acids. The preparation of 2,3,4,5-tetrafluorobenzoic acid is described, for example, in EP-A-0 510 490 or EP-A-0 140 482. Disadvantages of these preparation variants are, depending on the preparation method chosen, the necessity of going through complex, multistage synthesis sequences and the inevitable corrosion problems which result from the unavoidable formation of hydrogen fluoride which is released in the course of the synthesis.

There is therefore a need for new intermediates which enable 2-chloro-3,4,5-trifluorobenzoic acid to be prepared simply. These new intermediates should be able to be prepared simply and in high yields starting from readily accessible starting materials which are available in industrial quantities. Furthermore, it should also be made sure that the 2-chloro-3,4,5-trifluorobenzoic acid is obtained without great complexity, with a good yield and, at the same time, in high purity.

This object is achieved by substituted 2-chloro-3,4,5-trifluorobenzenes of the formula

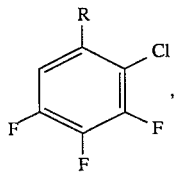

in which R is $NO_2$, $NH_2$, CN or Cl.

The present invention therefore relates to the compounds 2-chloro-3,4,5-trifluoronitrobenzene, 2-chloro-3,4,5-trifluoroaniline, 2-chloro-3,4,5-trifluorobenzonitrile and 2-chloro-3,4,5-trifluorochlorobenzene, in particular to 2-chloro-3,4,5-trifluoronitrobenzene, 2-chloro-3,4,5-trifluoroaniline and 2-chloro-3,4,5-trifluorobenzonitrile, preferably to 2-chloro-3,4,5-trifluoronitrobenzene and 2-chloro-3,4,5-trifluorobenzonitrile and, with particular preference, to 2-chloro-3,4,5-trifluorobenzonitrile.

The 2-chloro-3,4,5-trifluorobenzoic acid which is required for the preparation of 6,8-difluoroquinolinecarboxylic acids is obtained by converting 2-chloro-3,4,5-trifluoronitrobenzene into 2-chloro-3,4,5-trifluoroaniline and converting the latter to 2-chloro-3,4,5-trifluorobenzonitrile, and preparing 2-chloro-3,4,5-trifluorobenzoic acid from 2-chloro-3,4,5-trifluorobenzonitrile, for example by hydrolysis. However, it is also possible to convert 2-chloro-3,4,5-trifluoronitrobenzene into 2-chloro-3,4,5-trifluorochlorobenzene or 2-chloro-3,4,5-trifluorobromobenzene by way of 2-chloro-3,4,5-trifluoroaniline, and to use the 2-chloro-3,4,5-trifluorochlorobenzene or the 2-chloro-3,4,5trifluorobromobenzene to obtain, directly or following conversion to 2-chloro-3,4,5-trifluorobenzonitrile, the desired 2-chloro-3,4,5-trifluorobenzoic acid.

The present invention also relates to a process for the preparation of substituted 2-chloro-3,4,5-trifluorobenzenes of the formula

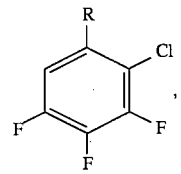

in which R is $NO_2$, $NH_2$, CN, Cl or Br. This process comprises reacting 2,3,4-trifluorochlorobenzene with a nitrating agent in the presence or absence of a water-insoluble solvent at from $-10°$ C. to $50°$ C., reducing 2-chloro-3,4,5-trifluoronitrobenzene or a mixture which contains 2-chloro-3,4,5-trifluoronitrobenzene and 5-chloro-2,3,4-trifluoronitrobenzene, in the presence of an organic solvent, isolating 2-chloro-3,4,5-trifluoroaniline or a mixture which contains 2-chloro-3,4,5-trifluoroaniline and 5-chloro-2,3,4-trifluoroaniline, diazotizing this product, if desired, and exchanging the diazotized group for a chloride atom, bromide atom or cyanide radical.

One advantage of the process according to the invention is the possibility of using 2,3,4-trifluorochlorobenzene as starting material. 2,3,4-Trifluorochlorobenzene can be prepared in a comparatively simple manner from a starting material which is already available in industrial quantities. Specifically, 2,3,4-trifluoronitrobenzene—which is accessible with comparative ease—is reacted under the conditions of denitrating chlorination to give the desired 2,3,4-trifluorochlorobenzene. The reaction proceeds smoothly to give the desired 2,3,4-trifluorochlorobenzene in good yield.

Employing 2,3,4-trifluorochlorobenzene under the conditions of an electrophilic substitution (for example Friedel-Crafts acylation or bromination) leads always to a mixture of different isomers, namely the corresponding (desired) 2-chlorinated product and the (unwanted) product in which the chlorine atom is in position 5. For instance, acylation using chloroacetyl chloride yields only 31% of 2-chloro-3,4,5-trifluorochloroacetophenone but not less than 69% of unwanted 5-chloro-2,3,4-chloroacetophenone (DE-A-41 23 322). The bromination of 2,3,4trifluorochlorobenzene gives a mixture which contains 2-chloro-3,4,5-trifluorobromobenzene and 5-chloro-2,3,4-trifluorobromobenzene in an approximate ratio of 50:50 (see also comparison example).

Against this background, it should be regarded as surprising that the procedure according to the invention, by means of nitration under conditions which are, comparatively, extremely mild yields a mixture in which the desired 2-chloro-3,4,5-trifluoronitrobenzene is the major product, at 75 % or more, while the unwanted 5-chloro-2,3,4-trifluoronitrobenzene is produced, at only 25 % or less, as by-product. Because the 2-chloro-3,4,5-trifluoronitrobenzene can be reduced to the corresponding 2-chloro-3,4,5-trifluoroaniline, which can be diazotized and subsequently converted by a Sandmeyer reaction into the corresponding 2-chloro-3,4,5-trifluorochlorobenzene or 2-chloro-3,4,5-trifluorobromobenzene, the present invention also gives highly selective access to both 2-chloro-3,4,5-trifluorochlorobenzene and 2-chloro-3,4,5-trifluorobromobenzene.

The figure below illustrates the individual reaction steps in diagrammatic form, including a possible means of reprocessing individual reaction products.

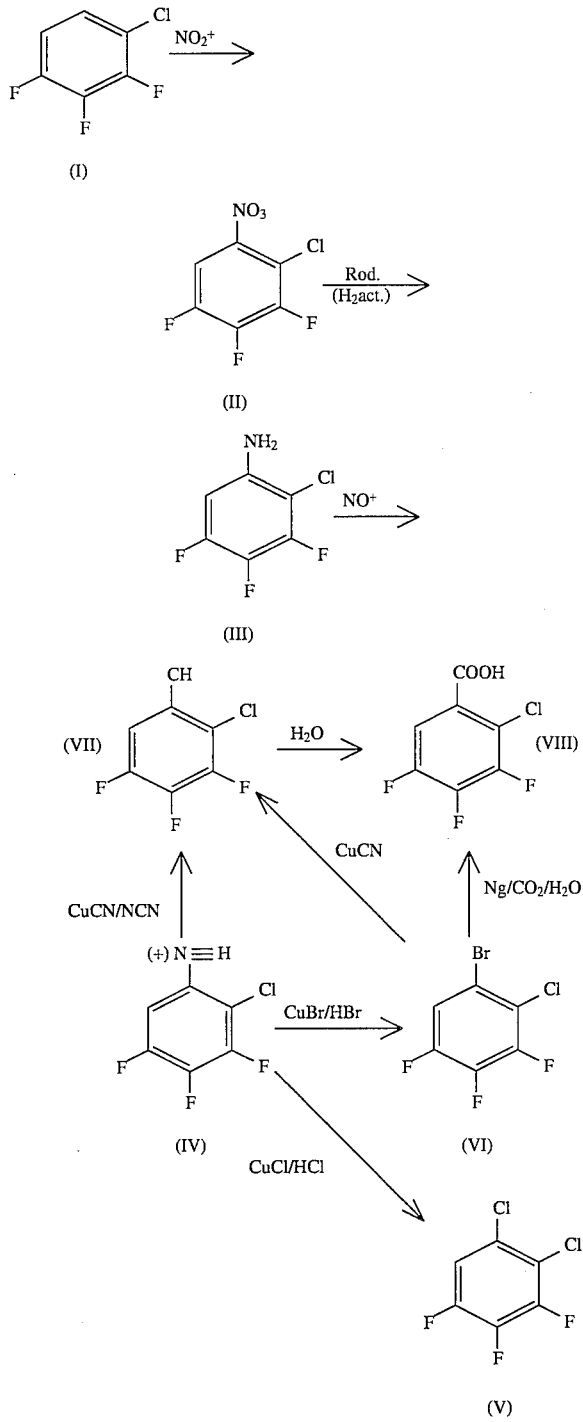

(I)   = 2, 3, 4-trifluorochlorobenzene
(II)  = 2-chloro-3, 4, 5-trifluoronitrobenzene
(III) = 2-chloro-3, 4, 5-trifluoroaniline
(IV)  = 2-chloro-3, 4, 5-trifluorodiazonium cation
(V)   = 2-chloro-3, 4, 5-trifluorochlorobenzene
        (1, 2-dichloro-3, 4, 5-trifluorobenzene)
(VI)  = 2-chloro-3, 4, 5-trifluorobromobenzene
(VII) = 2-chloro-3, 4, 5-trifluorobenzonitrile
(VIII)= 2-chloro-3, 4, 5-trifluorobenzoic acid 2,3,4-Trifluorochlorobenzene is first of all reacted with a nitrating agent which comprises or forms $NO_2^+$ as actual nitrating species. The nitrating agent commonly contains nitric acid, NO, $NO_2$, $N_2O_4$, and/or $N_2O_4$, dissolved if desired in sulfuric acid or oleum. A highly suitable nitrating agent is nitric acid dissolved in sulfuric acid or in oleum. Good success is generally achieved using nitrating agents which comprise from 2 to 100% by weight, in particular from 10 to 65% by weight and preferably from 15 to 40% by weight of nitric acid. The nitrating agent is advantageously employed to correspond to a molar ratio of nitric acid to 2,3,4-trifluorochlorobenzene of ( from 0.5 to 2.5 ): 1, in particular ( from to 1.5):1 and preferably (from 1.05 to 1.2):1. In this context, attention should be drawn to the fact that NO, $NO_2$, $N_2O_3$ and/or $N_2O_4$, especially $NO_2$, $N_2O_3$ and/or $N_2O_4$, also to a certain extent form nitric acid in the presence of water.

As already mentioned above, the nitration of 2,3,4-trifluorochlorobenzene can be carried out in the presence or absence of a water-insoluble solvent. An organic solvent which is inert under the reaction conditions of the nitration is used as water-insoluble solvent. Among such solvents, those which may be recommended are in general mono- or polychlorinated aliphatic hydrocarbons or mixtures thereof, especially mono- or polychlorinated aliphatic hydrocarbons of 1 to 8 carbon atoms, and mixtures thereof.

Highly suitable water-insoluble solvents are dichloromethane, chloroform, tetrachloromethane, 1,2-dichloroethane, mono- or polychlorinated aliphatic hydrocarbons of 1 to 4 carbon atoms, or mixtures of these compounds.

In general the quantity of water-insoluble solvent is of little importance. In most cases it is adequate to employ the water-insoluble solvent and 2,3,4-trifluorochlorobenzene in a weight ratio of (from 0.2 to 10):1, in particular (from i to 7.5):1 and preferably (from 1.5 to 5):1.

The nitration can be carried out, as already mentioned, at comparatively low temperatures. 2,3,4-Trifluorochlorobenzene is usually reacted with the nitrating agent at from −5° to 40° C., in particular from 0° to 30° C. Temperatures greater than 40° C. can also be employed, but no advantage is gained by this. The nitration may also be allowed to proceed at temperatures below −5° C., but a comparatively long reaction time must be accepted.

The nitration of 2,3,4-trifluorochlorobenzene produces a mixture which contains 2-chloro-3,4,5-trifluoronitrobenzene and 5-chloro-2,3,4-trifluoronitrobenzene. This mixture may advantageously be used, without dividing the compounds in a separate step, for the subsequent stage of reduction. If this procedure is adopted, the unwanted 5-chloro-2,3,4-trifluorobenzene derivative is separated off at a later point in time, for example at the stage of the aniline, nitrile, bromo or chloro compound, especially at the stage of the aniline or nitrile. It is, however, also possible to work up the 2-chloro-3,4,5-trifluoronitrobenzene-and 5-chloro-2,3,4-trifluoronitro-benzene-containing mixture, for example by fractional distillation, extractive distillation, melt crystallization, recrystallization or chromatography, or by a combination of these methods, and to employ 2-chloro-3,4,5-trifluoronitrobenzene in the subsequent stage of the reduction.

After the nitration, cold water is added if desired to the nitration mixture in order to dilute any sulfuric acid still present, after which an organic solvent which is inert to the conditions of the reduction is added to the nitrated product mixture in order to reduce it to the corresponding amine mixture. Suitable organic solvents are aliphatic hydrocarbons, cycloaliphatic hydrocarbons, aromatic hydrocarbons, aliphatic alcohols of 1 to 6 carbon atoms or alkyl esters of aliphatic carboxylic acids, formed from alkanols of 1 to 6 carbon atoms and aliphatic carboxylic acids of 1 to 6 carbon atoms. The reduction is advantageously carried out in the presence of one of these organic solvents or in the presence of a mixture of the abovementioned organic solvents.

Examples of suitable organic solvents which may be mentioned, in a list which makes no claim to completeness, are hexane, methylcyclohexane, toluene, o-xylene, m-xylene, p-xylene, mixtures of isomeric xylenes, methanol, ethanol, n-propanol, isopropanol, n-butanol, isobutanol methyl acetate, ethyl acetate, butyl acetate and/or 3-methoxybutyl butoxyacetate, especially toluene, o-xylene, m-xylene, p-xylene, mixtures of isomeric xylenes, methanol, ethyl acetate and/or buryl acetate. Mixtures of two or more of these organic solvents may also be used.

The reduction of the nitro group to the corresponding amino group can be carried out by a conventional method, as described, for example, in Houben-Weyl, Methoden der organischen Chemie [Methods of organic chemistry], Volume XI/1, pages 360 to 490. The reduction is particularly simple if it is carried out in the presence of a hydrogenation catalyst, using hydrogen or hydrazine, or using iron, a lower-valent sulfur compound, for example $H_2S$, a polysulfide or dithionite, tin, tin(II) chloride, iron(II) hydroxide or a hydrogen donor as reducing agent.

Suitable hydrogenation catalysts are the conventional transition metal-containing catalysts, which may comprise a support material or else may be free from a support.

The reduction is normally carried out using hydrogen at a pressure of from 0.05 to 20 MPa, in particular from 0.1 to 10 MPa and preferably from 0.2 to 8 MPa, in the presence of a hydrogenation catalyst which comprises nickel, platinum or palladium and, if desired, a support, at from 0° to 100° C., in particular from 40° to 90° C. Examples of support materials are alumina, pumice, active charcoal, silicic acid, kieselguhr, silica gel and $SiO_2$. Mixtures of the support substances mentioned above may also be used.

Examples of suitable hydrogenation catalysts are Raney nickel, Ni on kieselguhr or silicic acid, Pd and/or Pt on alumina, pumice or active charcoal, especially Pd on active charcoal and Pt on active charcoal, and preferably Pt on active charcoal. The nickel catalysts are used in quantities of from 0.5 to 5% by mass, especially from 1 to 4% by mass (calculated as nickel) and the noble metal catalysts in quantities of from 0.05 to 3% by weight, in particular from 0.3 to 1% by weight (calculated as pure transition metal), based in each case on the product to be hydrogenated. The catalysts may if desired be modified by appropriate additives, for example amines or $BaSO_4$, or by appropriate methods of treatment, for example partial poisoning.

When iron is used as reducing agent the reduction is generally carried out with the addition of an acid, especially a mineral acid such as HCl, $H_2SO_4$ or $H_3PO_4$. Another alternative is the method of so-called transfer hydrogenation (Houben-Weyl, Methoden der organischen Chemie [Methods of organic chemistry], Volume IV/1c, pages 67 to 76). In this case hydrogen donors are employed in place of hydrogen.

Examples of compounds which can be used as hydrogen donors are 1,3-cyclohexadiene, cyclohexene or hydrazine.

After the end of the reduction (hydrogenation) the catalyst is separated off, for example by filtration of the hot reaction product and the reaction product is concentrated and obtained by subsequent filtration or fractionation. In this context it is advisable, owing to the sensitivity of the resulting aniline derivatives to air, to add antioxidants, examples being hydrazine, hydrazinium salts or 2,6-di-tert-butyl-4-methylphenol.

After the end of the reduction the 2-chloro-3,4,5-trifluoroaniline- and 5-chloro-2,3,4-trifluoroaniline containing mixture or the 2-chloro-3,4,5-trifluoroaniline is usually isolated by distillation, melt crystallization, chromatography or simple phase separation (extraction). The method of isolation depends on the nature of the starting material and on the nature of the desired end product, and also on the degree of purity which is required in the end product. If the intention is to isolate a mixture containing 2-chloro-3,4,5-trifluoroaniline and 5-chloro-2,3,4-trifluoroaniline, then it is advisable to work up the crude reduced mixture by simple distillation. If, on the other hand, pure 2-chloro-3,4,5-trifluoroaniline is to be isolated from a 2-chloro-3,4,5- trifluoroaniline- and 5-chloro-2,3,4-trifluoroaniline containing mixture, then it is recommended to work up the crude reduced mixture by fractional distillation.

The mixture containing 2-chloro-3,4,5-trifluoroaniline and 5-chloro-2,3,4-trifluoroaniline, or the 2-chloro-3,4,5-trifluoroaniline, is subsequently diazotized using nitrous acid, or a substance which forms nitrous acid, at from −20° to 50° C., in particular from −10° to 30° C. The actual diazotizing species should be viewed as $NO^+$, which forms from nitrous acid.

5-Chloro-2,3,4-trifluoroaniline and/or 2-chloro-3,4,5-trifluoroaniline are reacted with nitrous acid in a molar ratio of 1:(from 0.9 to 10), in particular 1:(from 1 to 5) and preferably 1:(from 1.05 to 2). Examples of the diazotizing agents used are nitrosylsulfuric acid and alkali metal nitrites or alkaline earth metal nitrites in mineral acids, such as hydrochloric acid, sulfuric acid, hydrobromic acid and hydroiodic acid, from which nitrous acid is formed.

The diazotization transforms the original amino group into a diazotized group (diazonium group). In a subsequent step the diazotized group (diazonium group) is reacted with an alkali metal chloride, alkali metal bromide, alkali metal cyanide, alkaline earth metal chloride, alkaline earth metal bromide and/or alkaline earth metal cyanide in the presence of copper or a copper salt, and is exchanged for a chlorine atom, bromine atom or cyano radical (Sandmeyer reaction).

This reaction results in the desired 2-chloro-3,4,5-trifluorochlorobenzene (1,2-dichloro-3,4,5-trifluorobenzene), 2-chloro-3,4,5-trifluorobromobenzene and 2-chloro-3,4,5-trifluorobenzonitrile, which can be prepared either directly by substituting the diazotized group for a cyano radical, or by bromo-cyano exchange from 2-chloro-3,4,5-trifluorobromobenzene. 2-Chloro-3,4,5-trifluorobenzonitrile can be converted simply by hydrolysis into 2-chloro-3,4,5-benzoic acid, which in turn—as already detailed at the outset—can be used for the preparation of 6,8-difluoroquinolonecarboxylic acids.

The individual reaction steps can be carried out under atmospheric pressure, at subatomspheric pressure or at superatmospheric pressure.

The substituted 2-chloro-3,4,5-trifluorobenzenes of the formula

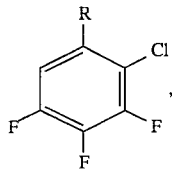

in which R is NO$_2$, NH$_2$, CN or Cl can be used as starting materials for the preparation of 2-chloro-3,4,5-trifluorobenzoic acid and antibacterial agents.

The examples which follow demonstrate the invention without limiting it.

EXAMPLE 1

2-Chloro-3,4,5-trifluoronitrobenzene 64.8 g (0.35 mol) of mixed acid prepared from 68.8% by weight of 100% strength H$_2$SO$_4$+31.2% by weight of 100% strength HNO$_3$ are added dropwise in 1 hour with cooling at 21° C. to an initial charge of 54.9 g (0.33 mol) of 2,3,4-trifluorochlorobenzene in 47.2 g (0.11 mol) of 20% strength oleum. The mixture is stirred for 30 min and hydrolyzed with 330 g of ice-water. The phases are separated (57.6 g of organic phase) and the aqueous phase is extracted by shaking with 65 g of toluene, giving 429.1 g of yellow aqueous phase and 66.2 g of yellow toluene phase. The combined organic phases are washed twice with 50 g of 10% strength sodium carbonate solution and then three times with 75 g of water. 117.7 g of organic phase are obtained, comprising 58.8 g (0.278 mol, 84%) of chlorotrifluoronitrobenzenes which may be separated by fractional distillation (isomer ratio of 2-chloro-3,4,5-trifluoronitrobenzene to 5-chloro-2,3,4-trifluorobenzene (NMR)=76:24) or else can be processed further as a mixture, with separation of the isomers taking place at a later stage.

If 0.15 mol of 2,3,4-trifluorochlorobenzene in 50 g of 100% strength sulfuric acid as diluent is used and nitration is carried out with 30.5 g (0.165 mol) of mixed acid prepared from 68.8% by weight of 100% strength H$_2$SO$_4$ and 31.2% by weight of 100% strength HNO$_3$ at from 5° to 12° C., then reaction is complete after metered addition for 1 hour followed by stirring for an additional hour. The result is essentially the same.

2-Chloro-3,4,5-trifluoronitrobenzene:

$^1$H-NMR (CDCl$_3$, TMS): δ=7.76 (g, 1H, J=2.25 Hz, J=6.84 Hz, J=9.16 Hz, Ar-H$^6$)

$^{19}$F-NMR (CDCl$_3$, CFCl$_3$):

$$\delta = -127.08(q, 1F, J = 2.25\ Hz, J = 4.7\ Hz, J = 19.7\ Hz, Ar-F^4)$$
$$-131.17(q, 1F, J = 7.4\ Hz, J = 9.16\ Hz, J = 20.8\ Hz, Ar-F^3)$$
$$-147.34(q, 1F, J = 6.84\ Hz, J = 19.7\ Hz, J = 20.8\ Hz, Ar-F^4)$$

$$MS:\ m/z\ (\%) = 61(12.3), 68(6.7), 9(8.6), 75(7.3), 79(10.1), 80(28.7), 91(7.9), 93(6.8), 99(23.6), 111(7.8), 115(81.9), 117(28), 130(29.7), 153(41.9), 155(14.3), 165(63.3), 167(21.3), 181(37.9), 183(12.3), 211(M^+, 100), 212(7.4), 213(33)$$

5-Chloro-2,3,4-trifluoronitrobenzene:

$^1$H-NMR (CDCl$_3$, TMS):

δ=8.07 (q, 1H, J=2.44 Hz, J=6.83 Hz, J=7.03 Hz, AR-H$^6$)

$^{19}$F-NMR (CDCl$_3$, CFCl$_3$)

$$\delta = -121.52(q, 1F, J = 6.83\ Hz, J = 14.6\ Hz, J = 19.32\ Hz, Ar-F^4)$$
$$-127.12(q, 1F, J = 7.03\ Hz, J = 14.6\ Hz, J = 20.6\ Hz, Ar-F^2)$$
$$-150.64(q, 1F, J = 2.44\ Hz, J = 19.32\ Hz, J = 20.6\ Hz, Ar-F^3)$$

$$MS:\ m/z\ (\%) = 61(14.7), 80(37.2), 99(30), 1515(97.2), 117(34.2), 130(36.2), 153(65.6), 155(21.7), 165(61.9), 167(20.4), 181(44.2), 183(16.3), 211(M^+, 100), 213(32.7)$$

EXAMPLE 2

2-Chloro-3,4,5-trifluoroaniline 117.7 g of the crude product from Example 1 (solution in toluene of 2-chloro-3,4,5-trifluoronitrobenzene and 5-chloro-2,3,4-trifluoronitrobenzene) are introduced as initial charge at 40° C. with 0.7 g of sulfited Pt/C catalyst. The reaction mixture is heated to 80° C. with a slight overpressure of hydrogen. The reduction is complete after 5 hours, and nitro compounds can no longer be detected by GC. The catalyst is filtered off, washing is carried out with 75 g of toluene, and the aqueous phase (5.6 g) is separated off from the filtrate. The major proportion of the toluene is distilled off at atmospheric pressure and the residue which remains is distilled at 1 mbar/80° C.–44.0 g (0.242 mol, 87%) are obtained of a mixture of the two isomeric chlorotrifluoroanilines (2-chloro-3,4,5-trifluoroaniline and 5-chloro-2,3,4-trifluoroaniline) as colorless solids (the anilines are present in the distillate in a ratio of 8:22). The anilines may also be separated by fractional distillation, in which case the desired 2-chloro-3,4,5-trifluoroaniline distills over first.

2-Chloro-3,4,5-trifluoroaniline:

IR: ν cm$^{-1}$]=680, 825, 880, 1045, 1075, 1125, 1200, 1250, 1470, 1520, 1615, 1645, 3430, 3520.

$^1$H-NMR (CDCl$_3$, TMS):

δ=6.38 (q, 1H, J=2.3 Hz, J=6.7 Hz, J=11.45 Hz, Ar-H$^6$ )

$^{19}$F-NMR (CDCl$_3$, CFCl$_3$):

$$\delta = -134.51(q, 1F, J = 2.3\ Hz, J = 6.1\ Hz, J = 21.2\ Hz, Ar-F^3)$$
$$-136.73(q, 1F, J = 6.1\ Hz, J = 11.45\ Hz, J = 21.8\ Hz, Ar-F^5)$$
$$-172.09(q, 1F, J = 6.7\ Hz, J = 21.2\ Hz, J = 21.8\ Hz, Ar-F^4)$$

MS: m/z (%) = 68(3.8), 69(6.9), 70(4.4), 75(7.3), 76 (3.8), 79(2.7), 80(3.4), 91(3.9), 93 (3.7), 94(3.7), 96(2.1), 99(13.7), 100 (2.8), 118(9.7), 119(33.8), 125(2.8), 126(16.0), 144(2.6), 145(10.5), 146 (11.9), 153(8.7), 154(3.3), 155(3.1), 161(2.8), 181($M^+$, 100), 182(7.9), 183(32.8)

5-Chloro-2,3,4-trifluoroaniline:
IR: ν [cm$^{-1}$]=705, 870, 1020, 1170, 1225, 1260, 1515, 1615, 1645, 3420, 3510
$^1$H-NMR (CDCl$_3$, TMS):
δ=6.56 (g, 1H, J=2.45 Hz, J=6.5 Hz, J=8.25 Hz, Ar-H$^6$)
$^{19}$F-NMR (CDCl$_3$, CFCl$_3$):

δ = −149.52($q$, 1F, $J$ = 1.0 Hz, $J$ = 6.5 Hz, $J$ = 21.0 Hz, Ar − F$^{4,2}$)
−157.13($q$, 1F, $J$ = 1.0 Hz, $J$ = 8.25 Hz, $J$ = 19.45 Hz, Ar − F$^{2,4}$)
−157.81($q$, 1F, $J$ = 2.45 Hz, $J$ = 19.45 Hz, $J$ = 21.0 Hz, Ar − F$^3$)

EXAMPLE 3 (comparison example)

111.9 g (0.7 mol) of bromine are added dropwise over 3.5 hours to an initial charge of 99.9 g (0.6 mol) of 2,3,4-trifluorochlorobenzene with 4 g (72 mmol) of iron at 100° C. The mixture is subsequently stirred at reflux until the total reaction time reaches 24 hours. After they have been cooled, the contents of the flask are carefully admixed with aqueous 10% strength sodium sulfite solution until the oxidizing effect of the solution is no longer evident. The organic phase is separated off, dried over magnesium sulfate, filtered and subjected to fractional distillation (initial quantity 127.2 g). The crude product contains 2-chloro-3,4,5-trifluorobromobenzene and 5-chloro-2,3,4-trifluorobromobenzene in a ratio of 59:41. The organic phase comprises 13.5% of dibromo compounds in addition to 18% of starting material and 68% of monobromo compounds (all GC, a/a). 74.7 g (0.337 mol, 56.6%) are obtained of the mixture of monobromo compounds with a purity>96% and with the isomer ratio as indicated. Including the amounts present in the intermediate and initial fractions, 86.1 g (65%) of a mixture of monobromo-chloro-trifluorobenzenes are obtained.

EXAMPLE 4

2-Chloro-3,4,5-trifluorobenzonitrile 94.5 g (0.59 mol) of copper sulfate are dissolved in 206 g of water. This solution is added with stirring to a solution prepared from 155 g of water, 65.0 g (1.0 mol) of potassium cyanide and 30.0 g (0.44 mol) of 25% strength ammonia solution. Cooling is carried out using an ice bath. A dark brown to dark green solution is obtained.

In a separate vessel, 92.6 g (0.51 mol) of 2-chloro-3,4,5-trifluoroaniline are added to 200 g of 30% strength hydrochloric acid, carrying out cooling with the addition of 100 g of ice. The temperature is adjusted to −10° C. by external cooling. 36.2 g (0.52 mol) of sodium nitrite in 60 g of water are added to this mixture with stirring and cooling. The yellow reaction mixture, which becomes viscous, is made up to 2 l with water, and stirring is continued for 15 min after the end of the metered addition.

The copper-containing solution prepared initially is poured onto ice, and then the diazonium salt solution is added to this mixture. When metered addition is complete, the resulting mixture is adjusted to a pH of 8 using 25% strength aqueous ammonia solution.

The mixture is extracted with dichloromethane to give an organic phase which comprises not only 2-chloro-3,4,5-trifluorobenzonitrile (62.3%) but also 10.4% of the aniline employed. The aniline is removed by multiple washing with 10% strength hydrochloric acid, and the remaining solution is subjected to fractional distillation. 54.3 g (0.283 mol, 56%) of 2-chloro-3,4,5-trifluorobenzonitrile are obtained as a pale yellowish solid (purity (GC)>95%).

2-Chloro-2,3,4-trifluorobenzonitrile:
$^1$H-NMR (CDCl$_3$, TMS):
δ=7.77 (ddd, 1H, $J_{AD}$=2.3 Hz, $J_{CD}$=7.6 Hz, $J_{BD}$=10.3 Hz, Ar-H6)
$^{19}$F-NMR (CDCl$_3$, CFCl$_3$):

δ = −129.2($ddd$, 1F, $J_{AD}$ = 2.3 Hz, $J_{AB}$ = 7.3 Hz, $J_{AC}$ = 20.5 Hz, Ar − F3)
−134.1($ddd$, 1F, $J_{AB}$ = 7.3 Hz, $J_{BD}$ = 10.3 Hz, $J_{BC}$ = 20.7 Hz, Ar − F5)
−148.8($ddd$, 1F, $J_{CD}$ = 7.36 Hz, $J_{AC}$ = 20.5 Hz, $J_{BC}$ = 20.7 Hz, Ar − F4)

The reaction proceeds analogously if the substantially isomerically pure aniline is replaced by the isomer mixture (see also Example 5).

EXAMPLE 5

1,2-Dichloro-3,4,5-trifluorobenzene 20 g (0.16 mol) of sodium sulfite and 40 g of sodium chloride are added to a solution of 82 g (0.2 mol) of copper sulfate pentahydrate to precipitate copper(I) chloride, which is dissolved in 100 ml of concentrated hydrochloric acid. 48.3 g (0.266 mol) of 2-chloro-3,4,5trifluoroaniline/5-chloro-2,3,4-trifluoroaniline (ratio 78:22 according to NMR) are added to this solution with stirring. The mixture is cooled to 10° C., and a solution of 30 g (0.352 mol) of potassium nitrite in 60 g of water is added dropwise. During the addition, the temperature of the mixture is maintained below 20° C. After the end of the metered addition, stirring is continued for 1 hour and then the mixture is heated at 80° C. for 30 min, then cooled and rendered alkaline with sodium hydroxide solution. The mixture of products is prepurified by steam distillation. The oily phase which separates out in the distillate is separated off and subjected to fractional distillation (41 g). 32.3 g (0,161 mol, 60%) are obtained of a 75:25 mixture of 1,2-dichloro-3,4,5-trifluorobenzene and 1,5-dichloro-2,3,4-trifluorobenzene.

We claim:
1. Substituted 2-chloro-3,4,5-trifluorobenzene of the formula

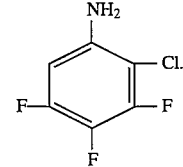

* * * * *